United States Patent [19]

Suwa et al.

[11] Patent Number: 5,344,764
[45] Date of Patent: Sep. 6, 1994

[54] PROTEIN INHIBITORS OF PHOSPHOLIPASE A2 PURIFIED FROM INFLAMMATORY SITES AND PRODUCTION PROCESS

[75] Inventors: Yorimasa Suwa, Tokyo; Atsushi Imaizumi; Masahiro Okada, both of Hino; Ichiro Kudo; Keizo Inoue, both of Tokyo; Yoji Suzuki, Hino, all of Japan

[73] Assignee: Teijin Limited, Osaka, Japan

[21] Appl. No.: 47,379

[22] Filed: Apr. 16, 1993

Related U.S. Application Data

[63] Continuation of Ser. No. 671,803, May 31, 1991, abandoned.

[30] Foreign Application Priority Data

Aug. 3, 1989 [JP] Japan .................................. 1-200246
Apr. 5, 1990 [JP] Japan .................................. 2-89085

[51] Int. Cl.$^5$ ........................ C12P 21/06; C12N 5/00; C12N 15/00; C07K 3/00
[52] U.S. Cl. ............................... 455/69.1; 435/240.2; 435/320.1; 530/350; 530/359; 530/361; 536/23.1; 536/23.2
[58] Field of Search .................. 435/69.1, 240.2, 320.1; 536/23.1, 23.2, 23.4, 23.5, 23.51, 23.7; 530/350, 359, 361

[56] References Cited

FOREIGN PATENT DOCUMENTS 63-500561 3/1988 Japan .
63-246397 10/1988 Japan .
291100 3/1990 Japan .

OTHER PUBLICATIONS

Davis, III et al., "Physiologic Inactivation of Fluid Phase C3b: Isolation and Structural Analysis of C3C C3d,g(α2D), and C3g", The Journal of Immunology, vol. 132, No. 4, Apr. 1984, pp. 1960–1966.

Proceedings of the National Academy of Sciences of USA, vol. 87, No. 7, pp. 2395–2399, Apr. 1990.

Pepinsky et al., "Five Distinct Calcium & Phospholipid Binding Proteins Share Homology with Lipocortin I*", The Journal of Biological Chemistry, vol. 263, No. 22, pp. 10799–10811 (Aug. 5, 1988).

Aarsman et al., "Lipocortin Inhibition of Extracellular and Intracellular Phospholipases A2 is Substrate Concentration Dependent", FEBS Letters, vol. 219, No. 1, pp. 176–180 (Jul. 1987).

Davidson et al., "Inhibition of Phospholipase A2 by Lipocortins and Calpactins", The Journal of Biological Chemistry, vol. 262, No. 4, pp. 1698–1705 (Feb. 5, 1987).

Suwa, Y., "Tanpakusitsu Kakusan Kouso", Proteins Nucleic Acids Enzymes, vol. 36, No. 3, pp. 333–341 (1991).

Misumi et al., "Nucleotide and Deduced Amino Acid Sequence of Rat Complement C3", Nucleic Acids Research, vol. 18, No. 8, p. 2178, Apr. 25, 1990.

Hellman, et al., "Amino Acid Sequence of the Trypsin-Generated C3d Fragment from Human Complement Factor C3", The Biochemical Journal, vol. 230, No. 2, pp. 353–361, Sep. 1, 1985.

Bruijn et al., "Human Complement Component C3: cDNA Coding Sequence and Derived Primary Structure", Proc. Natl. Acad. Sci. USA, vol. 82, pp. 708–712, Feb. 1985.

Pepinsky et al., (1986), JBC, vol. 261(9), pp. 4239–4246.

Primary Examiner—Robert J. Hill, Jr.
Assistant Examiner—Gian P. Wang
Attorney, Agent, or Firm—Sughrue, Mion, Zinn, Macpeak & Seas

[57] ABSTRACT

Protein inhibitors of phospholipase A2 purified from inflammatory sites which have an amino acid sequence given in FIGS. 3-1 through 3-3 or an amino acid sequence physiologically equivalent thereto, a process for preparation of said inhibitory protein wherein serum of mammalian animal is enzymatically treated, and a gene coding said inhibitory protein.

2 Claims, 31 Drawing Sheets

FIG. 1-1

| | | | | | | | | | | | |
|---|---|---|---|---|---|---|---|---|---|---|---|
|Glu|Asp|Val|Pro|Ala|Ala|Asp|Leu|Ser|Asp|Gln|Val 12|
|Pro|Asp|Thr|Asp|Ser|Glu|Thr|Arg|Ile|Leu|Leu|Gln|
|Gly|Thr|Pro|Val|Ala|Gln|Met|Ala|Glu|Asp|Ala|Val|
|Asp|Gly|Glu|Arg|Leu|Lys|His|Leu|Ile|Val|Thr|Pro|
|Ser|Gly|Cys|Gly|Glu|Glu|Asn|Met|Ile|Gly|Met|Thr 60|
|Pro|Thr|Val|Ile|Ala|Val|His|Tyr|Leu|Asp|Gln|Thr|
|Glu|Gln|Trp|Glu|Lys|Phe|Gly|Leu|Glu|Lys|Arg|Gln|
|Glu|Ala|Leu|Glu|Leu|Ile|Lys|Lys|Gly|Tyr|Thr|Gln|
|Gln|Leu|Ala|Phe|Lys|Gln|Pro|Ser|Ser|Ala|Tyr|Ala 108|
|Ala|Phe|Asn|Asn|Arg|Pro|Pro|Ser|Thr|Trp|Leu|Thr|
|Ala|Tyr|Val|Val|Lys|Val|Phe|Ser|Leu|Ala|Ala|Asn|
|Leu|Ile|Ala|Ile|Asp|Ser|Gln|Val|Leu|Cys|Gly|Ala|
|Val|Lys|Trp|Leu|Ile|Leu|Glu|Lys|Gln|Lys|Pro|Asp 156|
|Gly|Val|Phe|Gln|Glu|Asp|Gly|Pro|Val|Ile|His|Gln|

FIG. 1-2

Glu Met Ile Gly Gly Phe Arg Asn Thr Lys Glu Ala 180

Asp Val Ser Leu Thr Ala Phe Val Leu Ile Ala Leu

Gln Glu Ala Arg Asp Ile Cys Glu Gly Gln Val Asn

Ser Leu Pro Gly Ser Ile Asn Lys Ala Gly Glu Tyr

Leu Glu Ala Ser Tyr Leu Asn Leu Gln Arg Pro Tyr 228

Thr Val Ala Ile Ala Gly Tyr Ala Leu Ala Leu Met

Asn Lys Leu Glu Glu Pro Tyr Leu Thr Lys Phe Leu

Asn Thr Ala Lys Asp Arg Asn Arg Trp Glu Glu Pro

Gly Gln Gln Leu Tyr Asn Val Glu Ala Thr Ser Tyr 276

Ala Leu Leu Ala Leu Leu Leu Leu Lys Asp Phe Asp

Ser Val Pro Pro Val Val Arg Trp Leu Asn Glu Gln

Arg Tyr Tyr Gly Gly Gly Tyr Gly Ser Thr Gln Ala

Thr Phe Met Val Phe Gln Ala Leu Ala Gln Tyr Gln 324

Thr Asp Val Pro Asp His Lys Asp Leu Asn Met Asp

FIG. 1-3

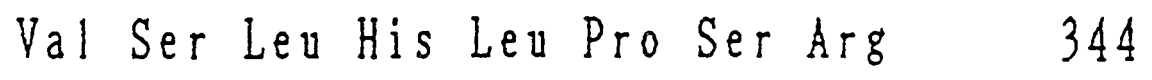

Val Ser Leu His Leu Pro Ser Arg      344

FIG. 2-1

```
GAG GAT GTA CCT GCA GCA GAC CTC AGT GAC CAA GTG      36

CCA GAC ACA GAT TCT GAG ACC AGA ATT CTC CTG CAA

GGG ACC CCG GTG GCT CAG ATG GCC GAC GAG GCT GTG

GAC GGG GAG CGG CTG AAA CAC CTG ATC GTG ACC CCC

TCT GGC TGT GGG GAG CAG AAC ATG ATT GGC ATG ACA     180

CCC ACG GTC ATT GCA GTA CAC TAT CTG GAT CAG ACC

GAA CAG TGG GAG AAA TTC GGC CTA GAG AAG AGG CAA

GAA GCT CTG GAG CTC ATC AAG AAA GGG TAC ACC CAG

CAG CTG GCT TTC AAA CAG CCC AGC TCT GCC TAT GCT

GCC TTC AAC AAC CGG CCT CCC AGC ACC TGG CTG ACA     360

GCC TAT GTG GTC AAG GTC TTC TCT CTG GCT GCC AAC

CTC ATC GCC ATC GAC TCT CAG GTC CTG TGT GGG GCT

GTC AAA TGG CTG ATT CTG GAG AAA CAG AAG CCA GAT

GGT GTC TTT CAG GAG GAC GGA CCA GTG ATT CAC CAA     504
```

FIG. 2-2

```
GAA ATG ATT GGT GGC TTC CGG AAC ACC AAG GAG GCA    540

GAT GTG TCG CTT ACA GCC TTT GTC CTC ATC GCA CTG

CAG GAA GCC AGA GAT ATC TGT GAG GGG CAG GTC AAC

AGC CTT CCC GGG AGC ATC AAC AAG GCA GGG GAG TAT

CTT GAA GCC AGT TAC CTG AAC CTG CAG AGA CCA TAC

ACA GTA GCC ATT GCT GGG TAT GCC CTG GCC CTG ATG    720

AAC AAA CTG GAG GAA CCT TAC CTC ACC AAG TTT CTG

AAC ACA GCC AAA GAT CGG AAC CGC TGG GAG GAG CCT

GGC CAG CAG CTC TAC AAT GTG GAG GCC ACC TCC TAC

GCC CTC CTG GCC CTG CTG CTG CTG AAA GAC TTT GAC

TCT GTG CCT CCT GTG GTG CGC TGG CTC AAC GAG CAA    900

AGA TAC TAC GGA GGT GGC TAT GGC TCC ACG CAG GCT

ACC TTC ATG GTA TTC CAA GCC TTG GCT CAA TAC CAA

ACA GAT GTC CCT GAC CAC AAG GAC TTG AAC ATG GAT   1008
```

FIG. 2-3

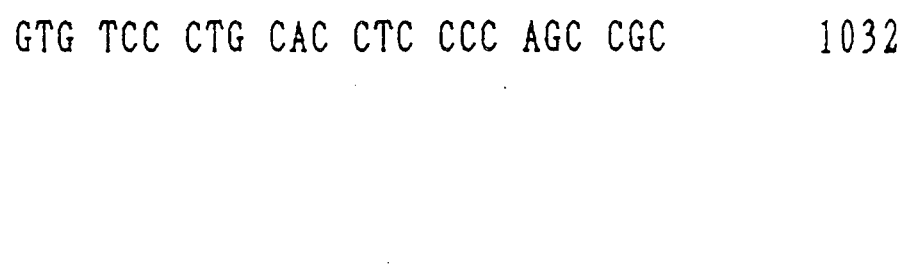

GTG TCC CTG CAC CTC CCC AGC CGC    1032

FIG. 3-1

Glu Gly Val Gln Lys Glu Asp Ile Pro Pro Ala Asp 12

Leu Ser Asp Gln Val Pro Asp Thr Glu Ser Glu Thr

Arg Ile Leu Leu Gln Gly Thr Pro Val Ala Gln Met

Thr Glu Asp Ala Val Asp Ala Glu Arg Leu Lys His

Leu Ile Val Thr Pro Ser Gly Cys Gly Glu Gln Asn 60

Met Ile Gly Met Thr Pro Thr Val Ile Ala Val His

Tyr Leu Asp Glu Thr Glu Gln Trp Glu Lys Phe Gly

Leu Glu Lys Arg Gln Gly Ala Leu Glu Leu Ile Lys

Lys Gly Tyr Thr Gln Gln Leu Ala Phe Arg Gln Pro 180

Ser Ser Ala Phe Ala Ala Phe Val Lys Arg Ala Pro

Ser Thr Trp Leu Thr Ala Tyr Val Val Lys Val Phe

Ser Leu Ala Val Asn Leu Ile Ala Ile Asp Ser Gln

FIG. 3-2

Val Leu Cys Gly Ala Val Lys Trp Leu Ile Leu Glu 156

Lys Gln Lys Pro Asp Gly Val Phe Gln Glu Asp Ala

Pro Val Ile His Gln Glu Met Ile Gly Gly Leu Arg

Asn Asn Asn Glu Lys Asp Met Ala Leu Thr Ala Phe

Val Leu Ile Ser Leu Gln Glu Ala Lys Asp Ile Cys 204

Glu Glu Gln Val Asn Ser Leu Pro Gly Ser Ile Thr

Lys Ala Gly Asp Phe Leu Glu Ala Asn Tyr Met Asn

Leu Gln Arg Ser Tyr Thr Val Ala Ile Ala Gly Tyr

Ala Leu Ala Gln Met Gly Arg Leu Lys Gly Pro Leu 252

Leu Asn Lys Phe Leu Thr Thr Ala Lys Asp Lys Asn

Arg Trp Glu Asp Pro Gly Lys Gln Leu Tyr Asn Val

Glu Ala Thr Ser Tyr Ala Leu Leu Ala Leu Leu Gln

FIG. 3-3

Leu Lys Asp Phe Asp Phe Val Pro Pro Val Val Arg 300

Trp Leu Asn Glu Gln Arg Tyr Tyr Gly Gly Gly Tyr

Gly Ser Thr Gln Ala Thr Phe Met Val Phe Gln Ala

Leu Ala Gln Tyr Gln Lys Asp Ala Pro Asp His Gln

Glu Leu Asn Leu Asp Val Ser Leu Gln Leu Pro Ser 348

Arg 349

FIG. 4-1

| | |
|---|---|
| GAA GGA GTG CAG AAA GAG GAC ATC CCA CCT GCA GAC | 36 |
| CTC AGT GAC CAA GTC CCG GAC ACC GAG TCT GAG ACC | |
| AGA ATT CTC CTG CAA GGG ACC CCA GTG GCC CAG ATG | |
| ACA GAG GAT GCC GTC GAC GCG GAA CGG CTG AAG CAC | |
| CTC ATT GTG ACC CCC TCG GGC TGC GGG GAA CAG AAC | 180 |
| ATG ATC GGC ATG ACG CCC ACG GTC ATC GCT GTG CAT | |
| TAC CTG GAT GAA ACG GAG CAG TGG GAG AAG TTC GGC | |
| CTA GAG AAG CGG CAG GGG GCC TTG GAG CTC ATC AAG | |
| AAG GGG TAC ACC CAG CAG CTG GCC TTC AGA CAA CCC | |
| AGC TCT GCC TTT GCG GCC TTC GTG AAA CGG GCA CCC | 360 |
| AGC ACC TGG CTG ACC GCC TAC GTG GTC AAG GTC TTC | |
| TCT CTG GCT GTC AAC CTC ATC GCC ATC GAC TCC CAA | |
| GTC CTC TGC GGG GCT GTT AAA TGG CTG ATC CTG GAG | 468 |

FIG. 4-2

```
AAG CAG AAG CCC GAC GGG GTC TTC CAG GAG GAT GCG    504

CCC GTG ATA CAC CAA GAA ATG ATT GGT GGA TTA CGG

AAC AAC AAC GAG AAA GAC ATG GCC CTC ACG GCC TTT

GTT CTC ATC TCG CTG CAG GAG GCT AAA GAT ATT TGC

GAG GAG CAG GTC AAC AGC CTG CCA GGC AGC ATC ACT

AAA GCA GGA GAC TTC CTT GAA GCC AAC TAC ATG AAC

CTA CAG AGA TCC TAC ACT GTG GCC ATT GCT GGC TAT    720

GCT CTG GCC CAG ATG GGC AGG CTG AAG GGG CCT CTT

CTT AAC AAA TTT CTG ACC ACA GCC AAA GAT AAG AAC

CGC TGG GAG GAC CCT GGT AAG CAG CTC TAC AAC GTG

GAG GCC ACA TCC TAT GCC CTC TTG GCC CTA CTG CAG

CTA AAA GAC TTT GAC TTT GTG CCT CCC GTC GTG CGT    900

TGG CTC AAT GAA CAG AGA TAC TAC GGT GGT GGC TAT    936
```

FIG. 4-3

GGC TCT ACC CAG GCC ACC TTC ATG GTG TTC CAA GCC    972

TTG GCT CAA TAC CAA AAG GAC GCC CCT GAC CAC CAG

GAA CTG AAC CTT GAT GTG TCC CTC CAA CTG CCC AGC    104

CGC    1047

Lane 1 HUMAN C3a (33kDa)
2 UNTREATED HUMAN SERUM (MAINLY ~100kDa)
3 HUMAN SERUM INCUBATED AT 37°C (MAINLY 39kDa)

FRACTION NUMBER         MARKER 45 48 51 54 57 60 63 66 69 kDa
— 66
— 42
— 31
— 24
— 14

FRACTION NUMBER         MARKER 9 10 11 12 13 14 15 16 17 18 19 kDa
— 66
— 42
— 31
— 24
— 14

FIG. 15b

FRACTION NUMBER    MARKER 16 17 18 19 20 21 22 23    kDa

FRACTION NUMBER      MARKER 23 24 25 26 27 28 29 30 31 32 kDa
—92
— —     —     —67
—45
— —    —31

FIG. 19

```
                          factor I
          275    280        ↓         290              300
HUMAN C3a   TLDPERLG[RE]GVQKEEIPPADLSDQVP RAT C3      TLDPEHLGQGGVQ[RE]DVPAADLSDQVP
                          ↑
                       factor I
```

```
                       factor I                    factor I
          625   630       ↓        640            650↓           660
HUMAN C3a   VSLQLPS[RS]SKIIHRIHWESAALL[RS]EETKENEGFTVTAEG RAT C3      VSLHLPS[RS]SPTVFRLLWESGSLL[RS]EETKQNEGFSLTAKQ
                    ↑                       ↑
```

FIG. 20

| a | b |
|---|---|
| SDS-PAGE MARKER | WESTERN BLOTTING MARKER |

```
     1   2                        1   2
            M.W.          M.W.
          — 92500
   —  — — 66200
          — 45000       45000—  —
   —
          — 31000       31000—
                                   —
          — 21500       21500—
          — 14400       14400—
```

Lane 1 REVERSE PHASE COLUMN FRACTION NUMBER 23

2 REVERSE PHASE COLUMN FRACTION NUMBER 30(C3dg)

PROTEIN INHIBITORS OF PHOSPHOLIPASE A₂ PURIFIED FROM INFLAMMATORY SITES AND PRODUCTION PROCESS

This is a continuation of application Ser. No. 07/671,803 filed May 31, 1991, now abandoned.

TECHNICAL FIELD

The invention relates to protein inhibiting phospholipase $A_2$ which participates in the progress of inflammation, the production process and gene therefor. More particularly, the invention concerns rat or human protein inhibitors of phospholipase $A_2$ purified from inflammatory sites.

BACKGROUND ART

Steroids have been used in treatment for a variety of inflammatory diseases as a powerful anti-inflammatory agent. Steroids have, however, various kinds of side-effects because of its hormonal actions and its application must be limited to relatively serious cases. Thus, the development of a novel drug having anti-inflammatory action comparative to that of steroids but much reduced side-effects has been most seriously awaited by the doctors treating inflammatory diseases.

As one of the mechanisms for steroids to manifest its anti-inflammatory action, it has been proposed that the synthesis of a protein which inhibits phospholipase $A_2$ is induced in the inflammatory site to suppress the production of arachidonic acid caused by the enzyme, resultantly the formation of the arachidonic acid metabolites having proinflammatory activity is lowered [Flower et al. Nature 278, 456, (1979)]. The phospholipase $A_2$-inhibitory protein has been expected to have the activity satisfactory for the above-stated requirements and numerous researchers have tried the isolation and purification of the protein, and the evaluation on its inflammatory action.

Until now, however, no protein having powerful actions comparative to steroids has been found and the following two reasons have been cited as the causes:

(1) In the previous researches, the enzyme purified from pancreas has been utilized in the evaluation system for activity inhibition, but the protein inhibitors of phospholipase $A_2$ purified from inflammatory sites has a different structure and different activities from phospholipase $A_2$ originating from pancreas, and (2) The inhibitor does not directly act on phospholipase $A_2$, and an apparent inhibitory activity by its interaction with the substrate has been detected.

The inventors paid attention to these problems and purified the phospholipase $A_2$ from the peritoneal exudate of rats with peritonitis caused by casein.

Additionally, the inventors have succeeded in purification of phospholipase $A_2$ from human inflammation sites, namely the synovial fluid in humans with rheumatoid arthritis [WO89/05851 specification (Japanese Patent 325255/(1987), Hara et al, J. Biochem. 104, 326–328 1988), and clarified that phospholipase $A_2$ purified from human inflammatory sites very well resembles phospholipase $A_2$ purified from rat inflammation region in the activity and structure. In other words, both enzymes showed high specificity to phosphatidylethanolamin. On the contrary, the phospholipase $A_2$ purified from pancreas does not exhibit such substrate specificity. The sequence of 34 amino acids on the N-terminal was compared and resultantly, the homology between the phospholipase $A_2$ purified from rat inflammation sites and the phospholipase $A_2$ purified from human inflammation sites was 67%, while it was only 45% between the phospholipase $A_2$ purified from human inflammatory sites and the phospholipase $A_2$ purified from pancreas.

In the meantime, the inventors have found a protein fraction which specifically inhibits the phospholipase $A_2$ purified from rat peritoneal exudate, in the peritoneal wash of the rats to which dexamethasone was given. The inventors purified the fraction to obtain proteins of about 35 kDa and 40 kDa and determined the amino acid sequence of individual N-terminals [Japanese Patent laid-open No. S 63-246397 (1988) (Japanese Patent Application No. S 62-79693 (1987)].

Further, the inventors obtained, as a protein specifically inhibiting phospholipase $A_2$ purified from synovial fluid of humans with rheumatoid arthritis, a protein of about 33 kDa as an enzymatic degradation products of human complement C3 and determined the amino acid sequence of the N-terminal (Japanese Patent Laid-open No. H 2-91100 (1990) (Japanese Patent Application No. S 63-242556 (1988)].

These inhibitory proteins did not exhibit the inhibitory activity against the pancreas phospholipase $A_2$ at all. In other words, these inhibitory proteins are quite unique because they have activities which have overcome the two above-mentioned problems and can be expected to manifest much more powerful anti-inflammatory action than that of the previously isolated phospholipase $A_2$-inhibitory protein.

The complete amino acid sequence of the protein inhibiting the phospholipase $A_2$ purified from inflammatory sites has not yet been elucidated. In addition, it is very extremely difficult to obtain a sufficient amount of the phospholipase $A_2$-inhibitory protein to evaluate the inflammatory action, when it is extracted and purified from the rat peritoneal wash or degradation products of human C3.

Meanwhile, according to the inventors, the N-terminal amino acid sequence of protein inhibitors of phospholipase $A_2$ purified from inflammatory sites, which has been purified from rat peritoneal wash, has extremely high homology with a part of the amino acid sequence of human complement C3α chain and is presumably a protein similar to C3 dg or C3d, a degradation product of C3.

It has been known that human complement C3 is cleaved stepwise by protease in serum into C3dg or C3d in the final stage. In addition, it has been reported that a high level of C3dg is detected in the synovial fluid of humans with rheumatoid arthritis by an immunochemical method and the values are correlated to the severity of the disease (Nydegger et al., J. Clin. Invest., 59, 862–868, 1977).

Previously, Japanese Patent Laid-open No. H 2-91100 (1990) described above is cited as a document relating to the correlation between the complement C3 and the phospholipase $A_2$-inhibitory protein purified from inflammatory sites. The patent document, however, does not describe the complete amino acid sequence and the gene of the inhibitory protein at all.

Further, there is no description of the correlation between said inhibitory protein and C3, particularly C3dg, a degradation product of complement C3, and of the preparation process for said inhibitory protein by enzymatic treatment of serum.

The object of the invention is to give the complete amino acid sequence of protein inhibitors of phospholipase A₂ purified from inflammatory sites clearly.

Another object of the invention is to clarify the DNA sequence coding the amino acid sequence of protein inhibitors of phospholipase A₂ purified from inflammatory sites and to provide the preparation process for giving a large amount of the protein.

DISCLOSURE OF THE INVENTION

The inventors have made intensified study, as considering the problems of prior arts, and reached the present invention by finding that a protein which is coded with 1032 bases and composed of 344 amino acids, and another protein which is coded with 1047 bases and composed of 349 amino acids, have inhibitory activity against phospholipase A₂ purified from inflammatory sites, respectively.

Namely, the present invention is protein inhibitors of phospholipase A₂ purified from inflammatory sites wherein said inhibitors have the amino acid sequence shown in FIG. 1 or an amino acid sequence physiologically equivalent thereto.

Further, the present invention is a production process for an inhibitory protein against phospholipase A₂ purified from inflammatory sites, said protein having the amino acid sequence given in FIG. 1 or amino acid sequences having physiologically equivalent thereto wherein said process comprises enzymatic treatment of mammalian serum.

The present invention is also a gene of the inhibitory protein against phospholipase A₂ purified from inflammatory sites wherein said protein has the amino acid sequence given in FIG. 1 or an amino acid sequence physiologically equivalent thereto.

Further, the present invention is an inhibitory protein against phospholipase A₂ purified from human inflammatory sites wherein said protein has the amino acid sequence given in FIG. 3 or an amino acid sequence physiologically equivalent thereto.

The present invention is a production process for an inhibitory protein against phospholipase A₂ purified from inflammatory sites, said protein having the amino acid sequence given in FIG. 3 or an amino acid sequence physiologically equivalent thereto wherein said process comprises enzymatic treatment of human serum.

Finally, the present invention is also a gene which codes the inhibitory protein against phospholipase A₂ purified from human inflammatory sites wherein said protein having the amino acid sequence given in FIG. 3 or an amino acid sequence physiologically equivalent thereto.

BRIEF DESCRIPTION OF THE DRAWINGS

FIGS. 1-1-1-3 give the amino acid sequence of the rat inhibitory protein-rat against phospholipase A₂ purified from inflammatory sites (abbreviated to inhibitory protein-rat) according to the invention.

FIGS. 2-1-2-3 give an example of DNA base sequence including the gene of the inhibitory protein-rat.

FIGS. 3-1-3-3 show the amino acid sequence of human phospholipase A₂-inhibitory protein purified from inflammatory site-human (abbreviated to inhibitory protein-human hereinafter) according to the present invention.

FIGS. 4-1-4-3 show an example of the DNA base sequence of the gene for the inhibitory protein-human according to the present invention.

FIGS. 15a–b depict an elution pattern (FIG. 15a) and SDS-PAGE (FIG. 15b) of the inhibitory protein-human in gel filtration HPLC.

FIGS. 16a–b depict an elution pattern (FIG. 16a) and SDS-PAGE (FIG. 16b) in reverse-phase HPLC.

FIG. 19 gives the amino acid sequence near the breakage site of rat C3 by factor I of human C3.

FIGS. 20a–b depict SDS-PAGE (FIG. 20a) and Western Blotting (FIG. 20b) of inhibitory protein-human according to the present invention.

BEST EMBODIMENT OF THE INVENTION

Figure 5:
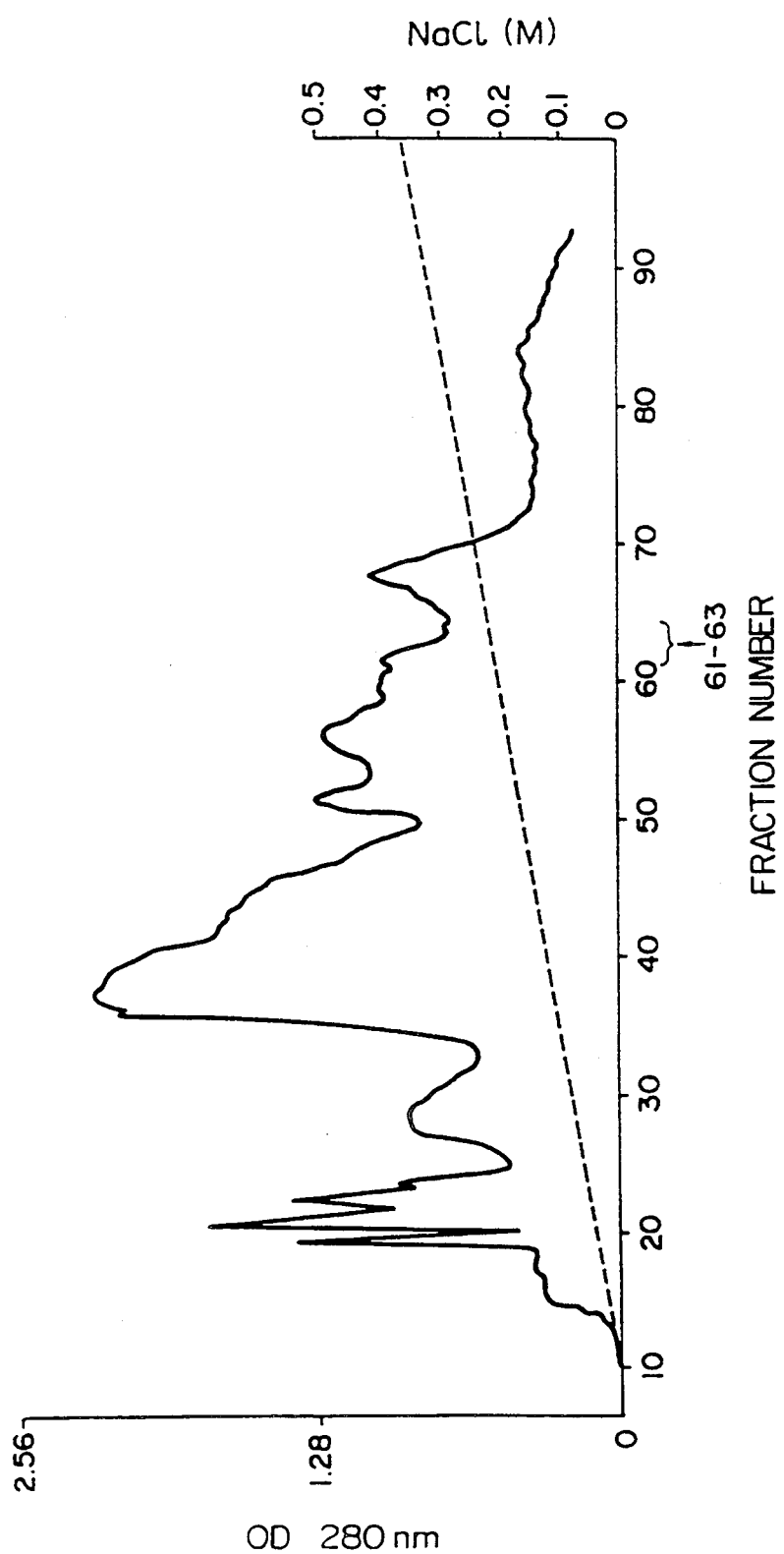
FIG. 5 depicts an elution pattern of the inhibitory protein-rat in anion-exchange HPLC.

The protein inhibitors of phospholipase A₂ purified from inflammatory sites according to the present invention is a polypeptide having the sequence of 344 amino acids given in FIGS. 1-1-1-3 or another one having the sequence of 349 amino acids given in FIGS. 3-1-3-3, and other polypeptides are also included in the protein inhibitors of phospholipase A₂ purified from inflammatory sites according to the present invention, as long as they have a substantially equal level of biological activity to the inhibitory protein-human, even when the amino acid sequence of the inhibitory protein is partially substituted, deleted or inserted.

In the preparative process according to the present invention, the protein inhibitors of phospholipase A₂ purified from inflammatory sites are produced by enzymatic treatment of serum from human, rat or the like and the enzymatic treatment means direct treatment of serum at 37° C. for 6 to 10 days or treatment of C3 purified from serum with Factor I by usual operations.

Further, the gene of protein inhibitors of phospholipase A₂ purified from inflammatory sites according to the present invention comprised the sequence of 1032 DNAs given in FIGS. 2-1-2-3 or of 1047 DNA given in FIGS. 4-1-4-3, and the single stranded DNA and the double stranded DNA consisting of the single stranded DNA and the complementally stranded DNA are also included in the scope of the present invention.

Other DNA are also included in the genes of protein inhibitors of phospholipase $A_2$ purified from inflammatory sites according to the present invention, as long as they code the amino acid sequence of the inhibitory protein, even when the DNA has a base sequence resulting from partial substitution, deletion or insertion of the bases in the inhibitory protein gene, or the DNA includes the above-stated base sequence or a part of the above-stated base sequence.

Then, the method according to the present invention will be illustrated for reaching the complete amino acid sequence of the protein inhibitors of phospholipase $A_2$ purified from inflammatory sites and the gene of the inhibitory protein of the invention.

The protein inhibitor of phospholipase $A_2$ purified from inflammatory sites of the invention is isolated and purified by heat-treating or enzymatically treating serum and subjecting the resultant sample to anion-exchange HPLC, gel filtration HPLC and reverse phase HPLC, as the activity of phospholipase $A_2$ purified from inflammatory sites is used as an index, as described by Vik [Vik, D. P. et al. J. Immunol., 134, 2571 (1985)].

The serum used in the invention is mammalian serum, particularly rat serum or human serum. Then, the sample which has been isolated and purified is determined its N-terminal amino acid sequence by the gas-phase protein sequencer (Applied Biosystem Co.).

The inventors had cloned a rat C3 cDNA, $\gamma$rC3/11 which harbored an about 2.7 kbp of insert DNA and was regarded to include the whole part of the gene coding the inhibitory protein according the present invention, which is presumably a protein analogue to human C3dg.

Hereupon, the base sequence of the clone was determined and the base sequence of the gene of the inhibitory protein was identified in the comparison with the N-terminal amino acid sequence of the inhibitory protein.

In the case of the human protein, the N-terminal amino acid sequence of the purified sample was determined to be identical to human C3dg. Thus, the complete base sequence of the gene of the inhibitory protein was determined on the basis of the base sequence of human C3 gene [de Bruijn et al., Proc. Natl. Acad. Sci. USA, 82, 708-712(1985)].

Then, the complete amino acid sequence of the inhibitory protein was determined from the entire base sequence.

The tests and measurement methods used in the present invention were as follows:

(1) Measurement of the inhibitory activity against phospholipase $A_2$ purified from inflammatory sites The phospholipase $A_2$ which was isolated and purified from the peritoneal exudate of rats with peritonitis caused by casein or from the synovial fluid of the humans with rheumatoid arthritis and the substrate was $^{14}$C-phosphatidylethanolamine (about 2,000 dpm/nmol. 1 mM) extracted from E. coli cultured in the presence of $^{14}$C-acetic acid.

As for the enzymatic reactions, an inhibitor sample and water were combined with 50 μl of 0.5M Tris-HCl (pH 9.0), 25 μl of 40 mM $CaCl_2$ and 25 μl of the substrate to adjust the total volume to 240 μl. They were mixed, finally 10 μl of an enzyme solution (0.1 ng/μl) was added to the mixture to start the reactions at 37° C. for 10 minutes and the Dole's reagent was added (1.5 ml) to stop the reactions. According to the Dole's method, $^{14}$C-fatty acid was extracted and the radioactivity was measured with a liquid scintillation counter.

(a) SDS-polyacrylamide gel electrophoresis and Western blotting

One tenth volume of a dye solution (0.1% BPB, XC, 10% SDS) was added to a sample obtained from the enzymatic treatment or HPLC, they were heat-treated at 100° C. for 5 minutes, applied to 12.5% polyacrylamide gel and electrophoresed in the presence of 1% SDS with 15 to 25 mA for 1.5 hours. For analysis under reductive conditions, 2-mercaptoethanol (2ME) was added to the sample. After electrophoresis, the mixture was stained with CBB to detect the protein.

For the western blotting after electrophoresis, the protein was transferred from the gel to a nitrocellulose filter using an electroblot apparatus (Millpore Co.). Sheep anti-human C3d serum (Dako), horseradish peroxidase-conjugated anti-sheep IgG antibody (Cappel) and 4-chloro-1-naphthol (Bio-Rad) as a substrate were used to detect the C3d band by the enzyme-linked immunmostaining assay.

(3) Determination of N-terminal amino acid sequence of protein

A gas-phase protein sequencer (Applied Biosystem 477A) and HPLC (Applied Biosystem 120A) were employed.

In other words, 100 μl of a sample dissolved in 0.1% TFA was applied to the gas-phase protein sequencer. The protein underwent automatic Edmann degradation and the PTH (phenylthiohydantoin) amino acid derivatives were analyzed in the form of amino acids by high performance liquid chromatography.

(4) Determination of C-terminal amino acid sequence of protein

About 150 μg of a sample was dissolved in 100 μl of 8M urea-125 mM Tris.HCl buffer (pH 7.6), 2 μl of 2-mercaptoethanol was added and they were allowed to stand at 37° C. for 4 hours. Then, 2 μl of 4-vinylpyridine was added to start the reaction at 37° C. for 45 minutes. The sample was desalted by reverse phase HPLC (Vydac 218TP54) and freeze-dried. The sample was dissolved in 200 μl of 8M urea-1% ammonium hydrogencarbonate solution, 600 μl of 1% ammonium hydrogencarbonate solution was added to the solution, then 1 μg of α-chymotrypsin was added to start the reaction at 37° C. for 16 hours. Since the C-terminal of the protein was anticipated to be Arg, chymotrypsin was used.

Acetic acid was added to the reaction mixture to adjust the pH to about 5, and applied to an anhydrochymotrypsin agarose column (TAKARA SHUZO) which was equilibrated with 50 mM sodium acetate buffer (pH 5.0) containing 20 mM of $CaCl_2$.

The C-terminal fragment was recovered in the flow-through and its amino acid sequence was determined as in (3) to reveal the C-terminal amino acid sequence of the inhibitory protein.

The protein inhibitors of phospholipase $A_2$ purified from inflammatory sites according to the invention was elucidated on its complete amino acid sequence by the present invention, and can be produced by known methods of chemical synthesis, but the protein can be readily mass-produced by the recombinant DNA method.

The protein inhibitors of phospholipase $A_2$ purified from inflammatory sties will be utilized as an anti-inflammatory agent as well as in diagnosis of inflammatory diseases using an antibody obtained from the protein as an antigen or a kit for such diagnosis.

EXAMPLE

The present invention will be illustrated by the following examples in more detail.

EXAMPLE 1

Preparation of protein inhibitors of phospholipase $A_2$ purified from rat inflammatory sites (abbreviated to inhibitory protein-rat) and the measurement of the inhibitory activity (A) Preparation of inhibitory protein-rat (1) 0.1% of $NaN_3$ was added to rat serum (Japan Biomaterial) and treated at 37° C. for 10 days. Protease inhibitor (20 μg/ml aprotinin, 10 μg/ml soybean trypsin inhibitor, 0.5 mM EDTA) was added and the product was dialyzed twice against 3 liters of 20 mM Tris.HCl (pH 7.5).

(2) the dialyzed sample from (1) (protein concentration: about 30 mg/ml) was diluted 20 times, centrifuged to remove insoluble substance and the target protein was isolated and purified as follows:

First, the sample was fractionated with a preparative anion-exchange HPLC column (TSK gel DEAE-5PW) (FIG. 5).

In FIG. 5, the continuous line draws the UV absorptions at 280 nm wavelength and the dotted line shows the gradient of NaCl concentration.

The elution was conducted with 20 mM Tris.HCl, pH 7.5–NaCl (0→0.35 M) 2.5 ml/min, 2 min./tube. The column measured 21.5φ×30 cm.

Figure 6:
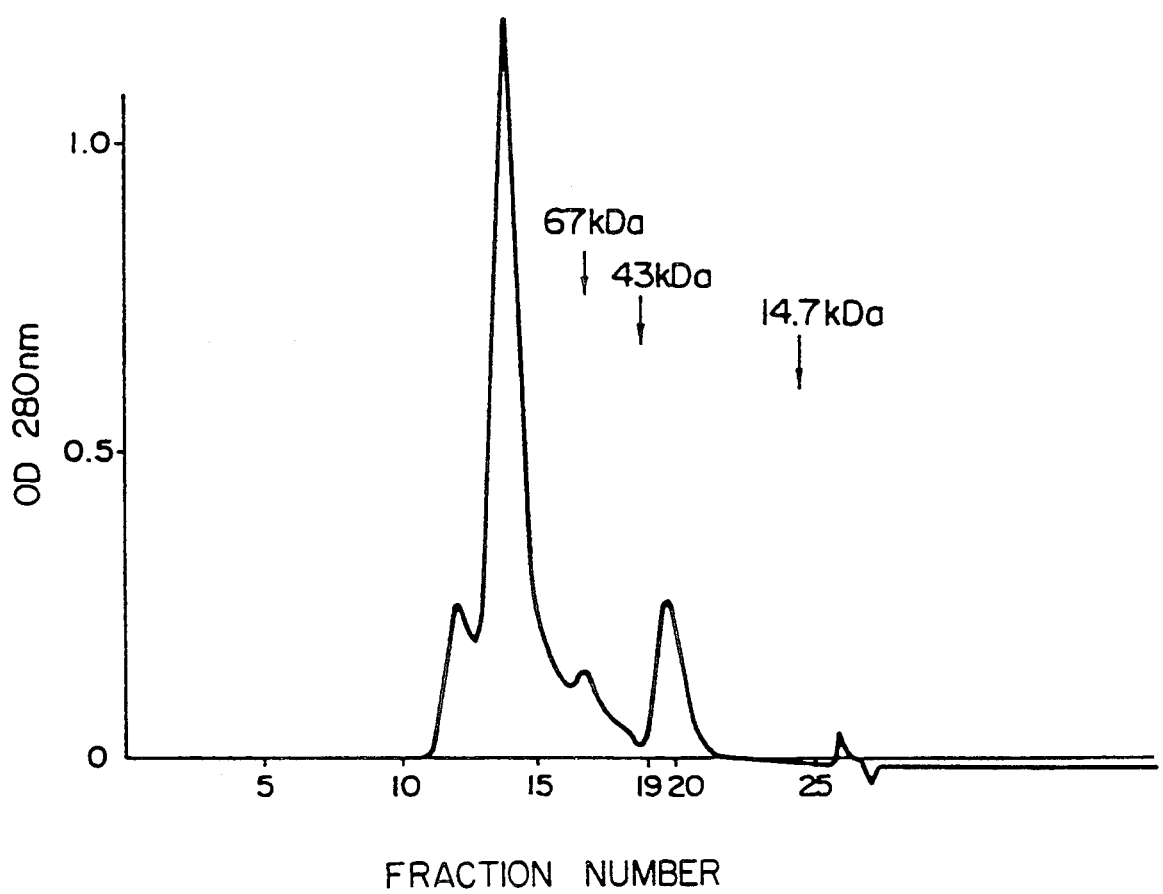
FIG. 6 depicts an elution pattern of the inhibitory protein-rat in gel filtration HPLC.

Then, the fractions Nr. 61 to 63 in which the 39 kDa band was detected in SDS-PAGE in FIG. 5 were collected, concentrated, and further fractionated with a gel filtration HPLC column (TSK gel G3000SW) (FIG. 6). In FIG. 6, the continuous line draws UV absorptions at 280 nm and the arrow marks give the elation positions of molecular weight markers.

The elution conditions were 20 mM Tris.HCl, pH 7.5–1 M NACl, 0.5 ml/min. 2 min./tube.

Figure 7:
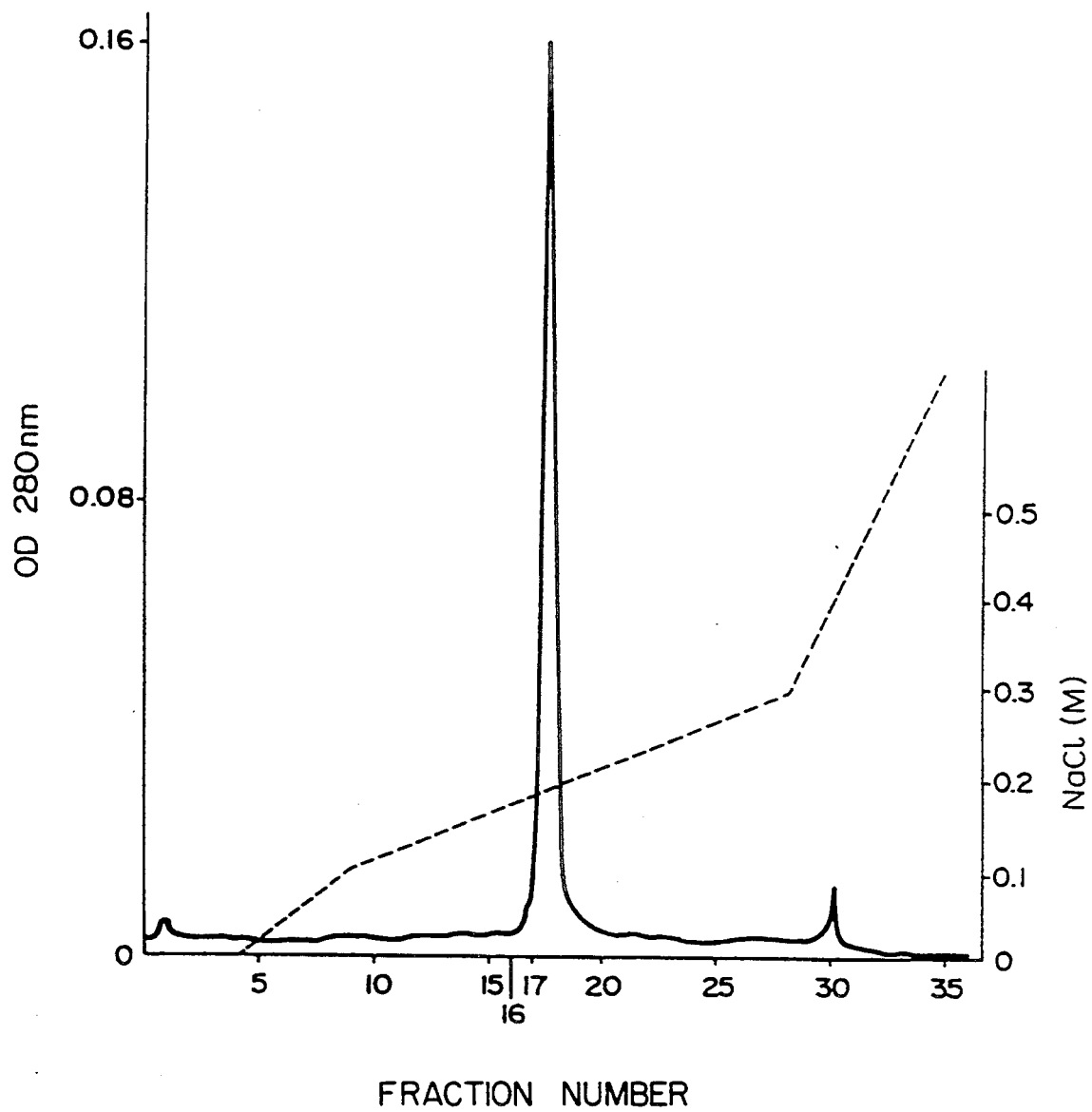
FIG. 7 depicts an elution pattern of the inhibitory protein-rat in anion-exchange HPLC.

Then, the fraction peaks Nr. 19 to 20 in which 39 kDa band was detected in SDS-PAGE in FIG. 6 were collected and purified with a preparative anion exchange HPLC column (TSK gel DEAE-SPW) (FIG. 7). In FIG. 7, the continuous line draws the UV absorptions at 280 nm and the dotted line shows the gradient of NaCl concentration.

The purification was conducted with 20 mM Tris.HCl, pH 7.5-NaCl (0→1.0 M) 1.0 ml/min, 2 min./tube.

Figure 8:
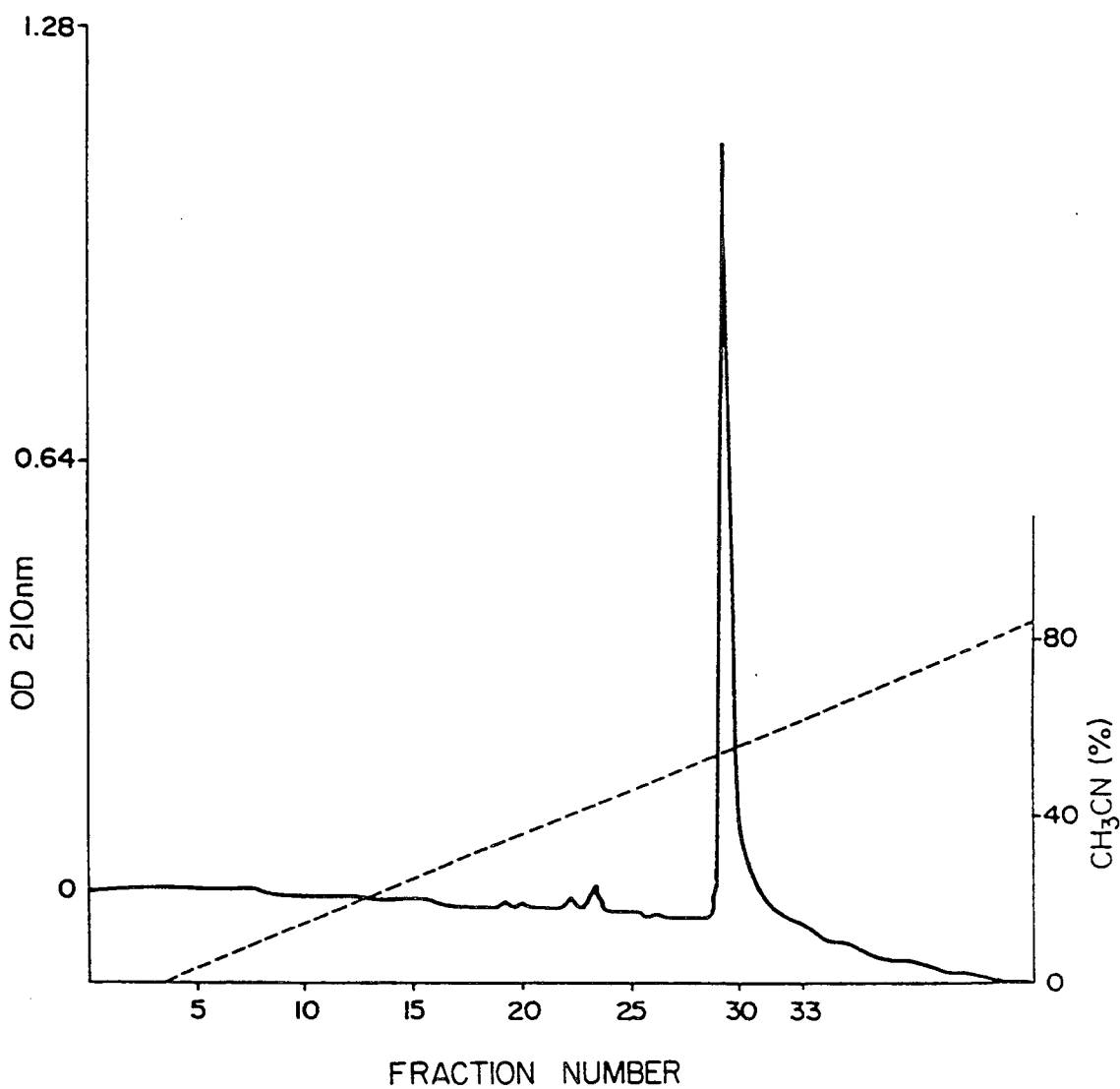
FIG. 8 depicts an elution pattern of the inhibitory protein-rat in reversed phase HPLC.

Finally, the main peak fraction Nr. 16 in FIG. 7 was further purified with a reversed phase HPLC column (Bio-Rad RP304) (FIG. 8). In FIG. 8, the continuous line draws the UV absorptions at 210 nm and the dotted line shows the gradient of the $CH_3CN$ concentration.

The purification was conducted with 0.1% TFA/$CH_3CN$ 0–80% 1 ml/min., 2 min./tube.

Figure 9:
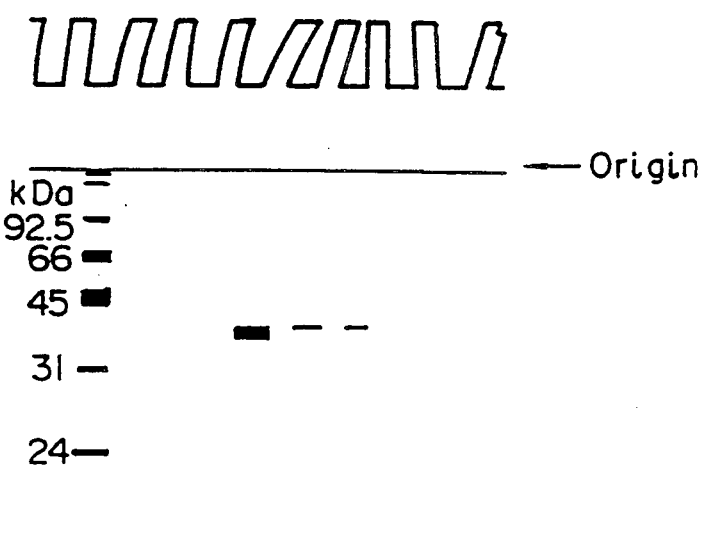
FIG. 9 gives SDS-PAGE of the inhibitory protein-rat.

The inhibitory protein-rat, obtained as described above, (fraction Nr. 30) showed a single band in SDS-PAGE (estimated molecular weight: about 39 kDa) (FIG. 9). SDS-PAGE was carried out after the fractions 29 to 33 was concentrated 10 times, respectively.

(B) phospholipase $A_2$-inhibitory activity of the inhibitory protein-rat

The inhibitory protein according to the present invention, obtained in (A) (fraction Nr. 30 in reversed phase HPLC, protein concentration 40 μg/ml) was determined its inhibitory activity against phospholipase $A_2$ purified from inflammatory sites and other phospholipase $A_2$ by the procedures for determining the inhibitory activity as described above (rat platelet-secretory phospholipase $A_2$ was used as an enzyme. It is same as phospholipase $A_2$ purified from inflammatory sites).

(1) In order to examine the inhibitory activity of the inhibitory protein according to the present invention against rat-phospholipase $A_2$, various amounts of the inhibitory protein were examined (3, 6, 9, 12, 15 and 18 ng). The results are given in FIG. 10.

Figure 10:
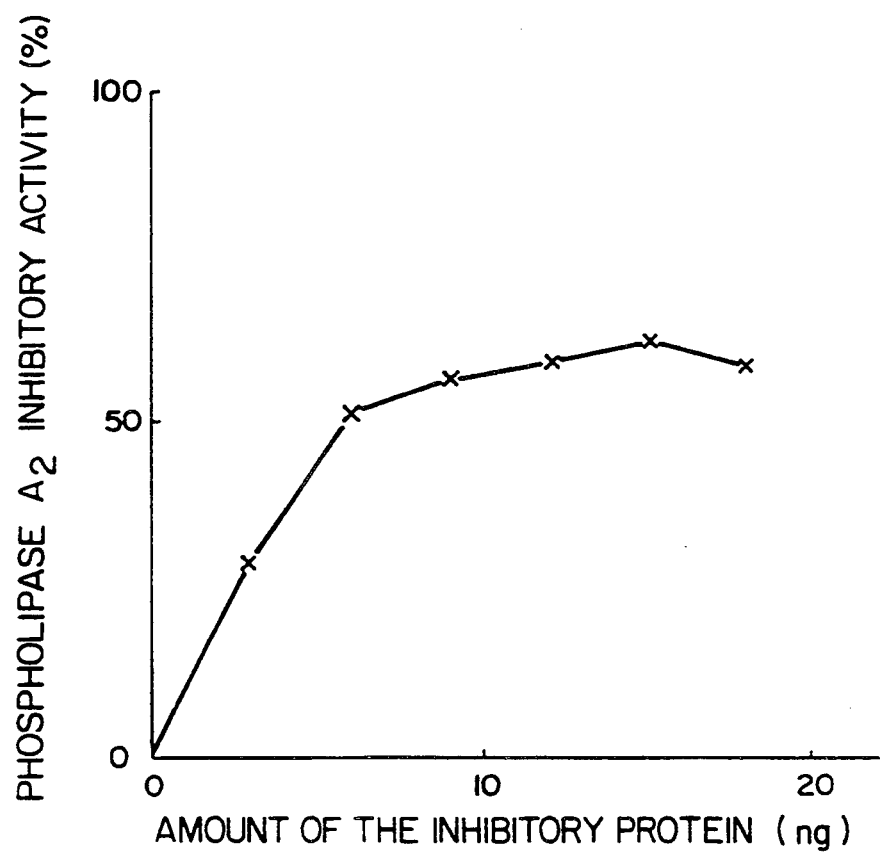
FIG. 10 shows the inhibitory activity of the inhibitory protein-rat according to the present invention.

FIG. 10 clearly shows that the inhibitory protein according to the invention inhibits the phospholipase $A_2$ purified from rat inflammatory sites in a dose dependent manner. The amount of the inhibitory protein which is needed for inhibiting 50% activity of 1 ng phospholipase $A_2$ was about 6 ng and $IC_{50}$ was $0.8 \times 10^{-9}$ M.

(2) In addition to phospholipase $A_2$ purified from rat inflammatory site, phospholipase $A_2$ purified from synovial fluid from humans with rheumatoid arthritis, phospholipase $A_2$ originating from Crotalus adamanteus venom (a snake venom) (Sigma Co.), porcine pancreas phospholipase $A_2$ (Sigma Co.), Naja naja venom (a snake venom) phospholipase $A_2$ (Sigma Co.) were used to determine the inhibitory activity of the inhibitory protein according to the present invention. The results are shown in FIG. 11a and FIG. 11b, respectively.

Figure 11A:
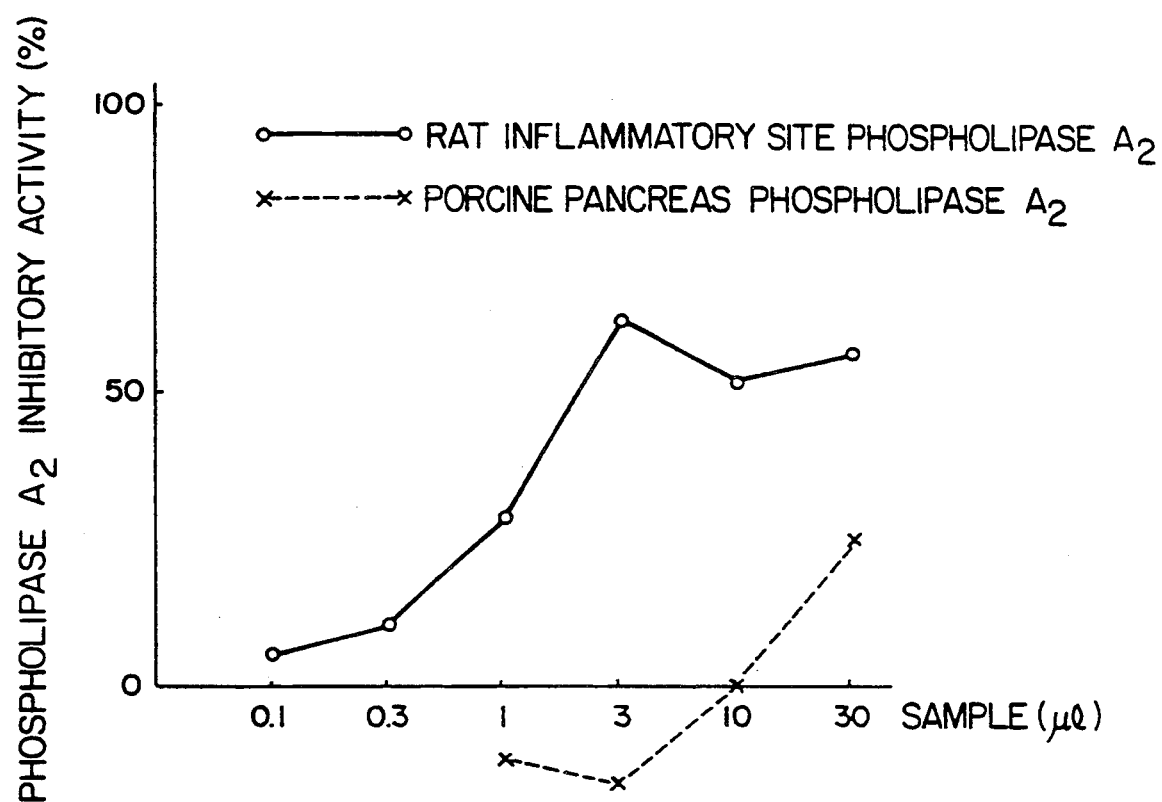
FIGS. 11a–b (including 11a and 11b) give the inhibitory activity of the inhibitory protein-rat according to the present invention against a variety of phospholipase A₂.
Figure 11B:
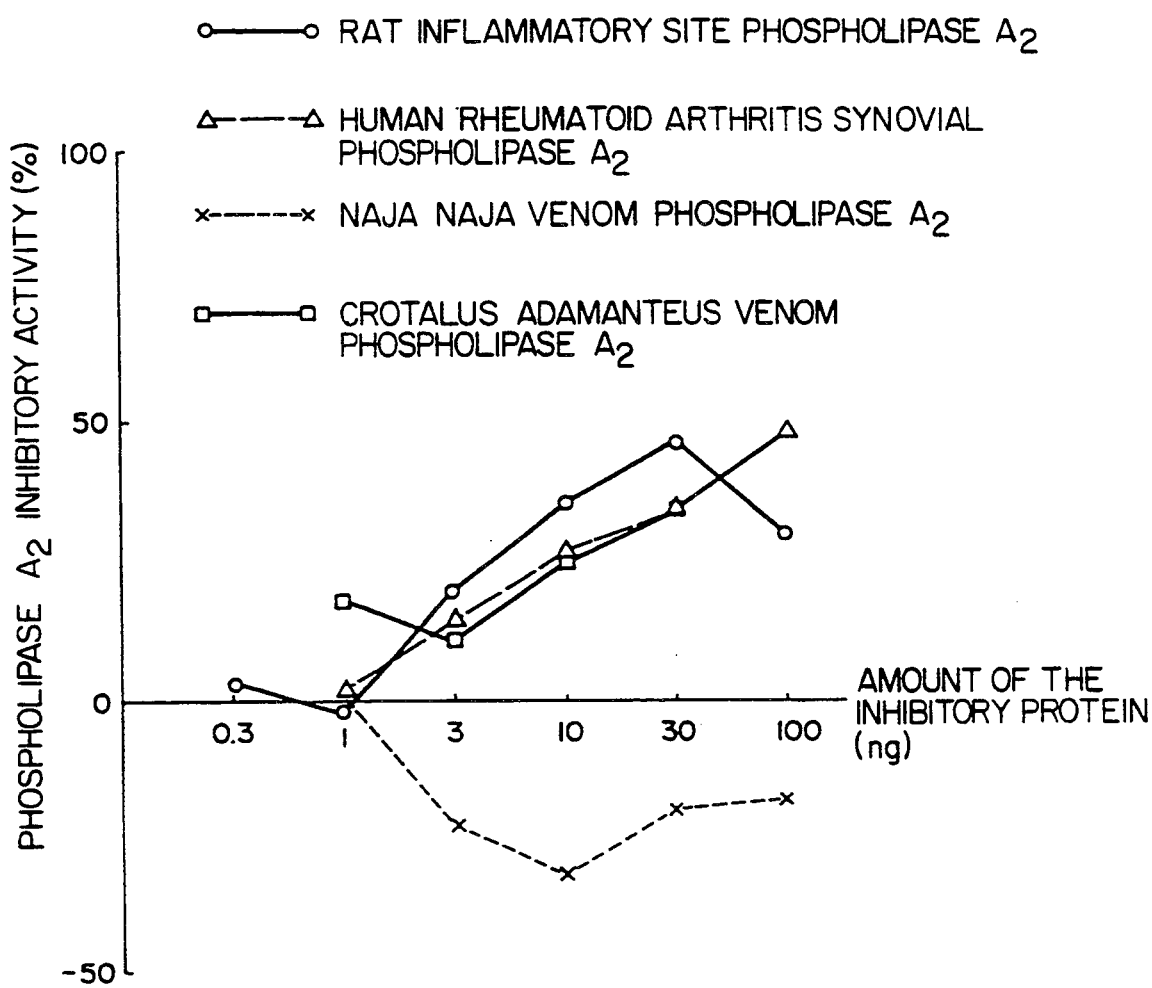

As shown in FIGS. 11a–b, the inhibitory protein manifested an almost equal level of inhibitory activity against phospholipase $A_2$ purified from rat inflammatory site (○-○) and that purified from the synovial fluid of humans with rheumatoid arthritis (Δ-Δ), and Crotalus adamanteus venom phospholipase $A_2$ (□-□), but revealed no activity against porcine pancreas phospholipase $A_2$ (x-x) and Naja naja venom phospholipase $A_2$ (x . . . x). Thus, it has been clarified that the inhibitory protein according to the present invention is specifically active against phospholipase $A_2$ purified from inflammatory sites.

(3) The inhibitory protein obtained in (A) revealed no change in its inhibitory activity, even when the substrate concentration in the assay system was changed from 0.1 to 0.35 mM. Further, the inhibitory protein was pre-incubated together with the enzymes before the assay, but no change was noticed in the activity.

These results indicated that the activity of the inhibitory protein is not caused by the interaction with the substrate.

(4) Consequently, it has been clearly shown that the inhibitory protein has almost the same molecular weight and the same level of activity as of protein inhibitors of phospholipase $A_2$ purified from inflammatory sites from rat peritoneal cavity.

EXAMPLE 2

Preparation of protein inhibitors of phospholipase $A_2$ purified from human inflammatory sites (abbreviated to inhibitory protein-human) and the measurement of its inhibitory activity (A) Preparation of inhibitory protein-human (1) 30 ml of human serum was mixed with 0.1% $NaN_3$ and incubated at 37° C. for 10 days.

Figure 12:
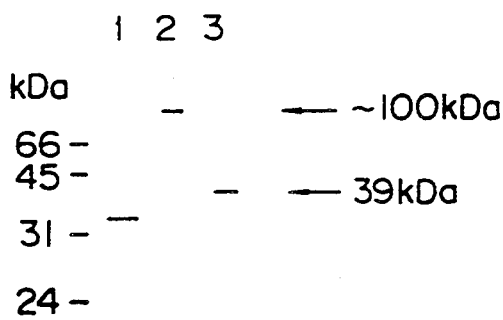
FIG. 12 gives Western blotting results of untreated and 37° C.-treated human serums.

Treated and untreated samples were diluted 50 times, respectively, subjected to SDS-PAGE and transferred to filters by the western blotting method. Each filter was subjected to the enzyme-linked immunostaining method using anti-human C3d serum, and only more than 100 kDa band was detected in the untreated serum, while only 39 kDa band, in the serum treated at 37° C. (FIG. 12). These results proved that the treatment at 37° C. caused cleavage of C3 by enzyme in serum to produce C3dg.

Hereupon, protease inhibitor (20 μg/ml aprotinin, 10 μg/ml soybean trypsin inhibitor, 0.5 mM EDTA) was added, and the mixture was dialyzed twice against 3 liters of 20 mM Tris.NaCl.

Figure 13A:
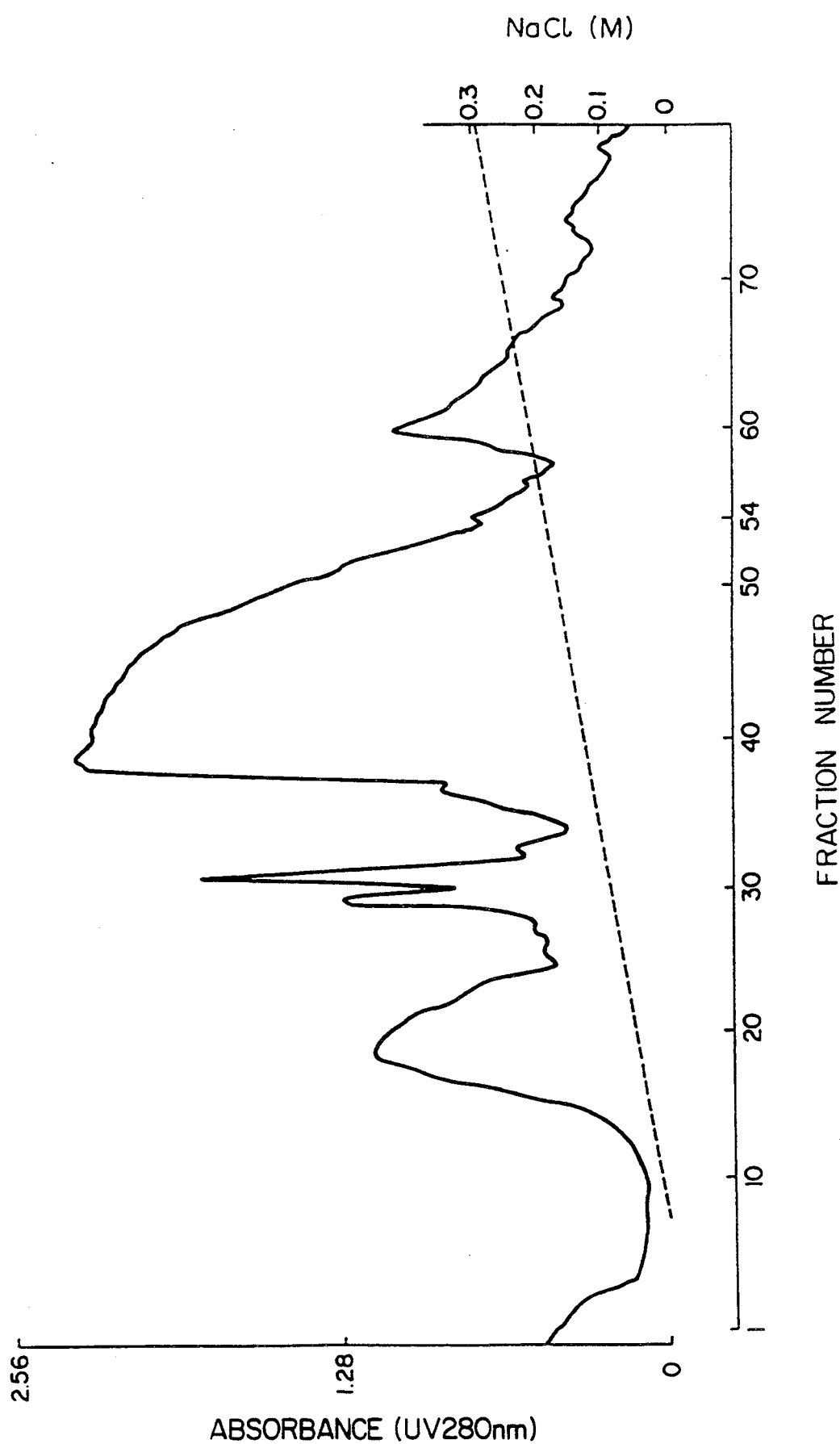
FIGS. 13a–b depict an elution pattern (13a) and SDS-PAGE (13b) of the inhibitory protein-human in preparative anion-exchange HPLC.
Figure 13B:
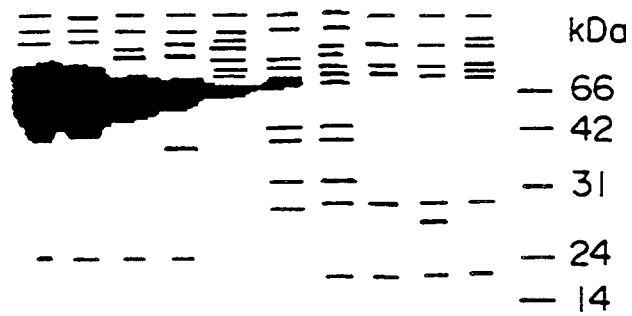

(2) The dialyzed sample obtained in (1) (protein concentration: about 30 mg/ml) was diluted 20 times, insoluble substances were removed by centrifugation and the target protein was isolated and purified as follows:

First, the sample was fractionated with an preparative anion exchange HPLC column (TSK gel DEAE-5PW) (FIGS. 13a–b). In FIG. 13a, the continuous line depicts the absorption at 280 nm, while the dotted line gives the NaCl concentration gradient. The elution was conducted under the conditions of 20 mM Tris.HCl, pH 7.5–NaCl (0→0.35 M), 2.5 ml/mlin, 2 min/tube. The column measured 21.5 mm$\phi$×30 cm.

Figure 14B:
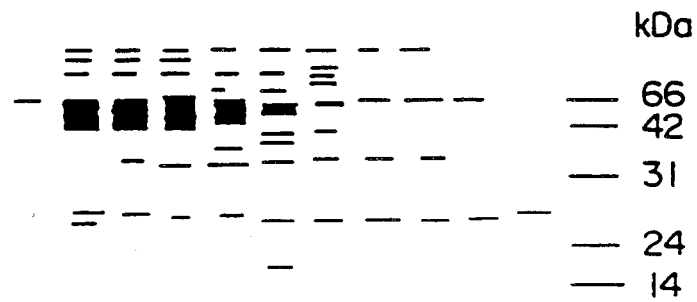
FIGS. 14a–b depict an elution pattern (14a) and SDS-PAGE (14b) of the inhibitory protein-human in analytical anion-exchange HPLC.
Figure 14A:
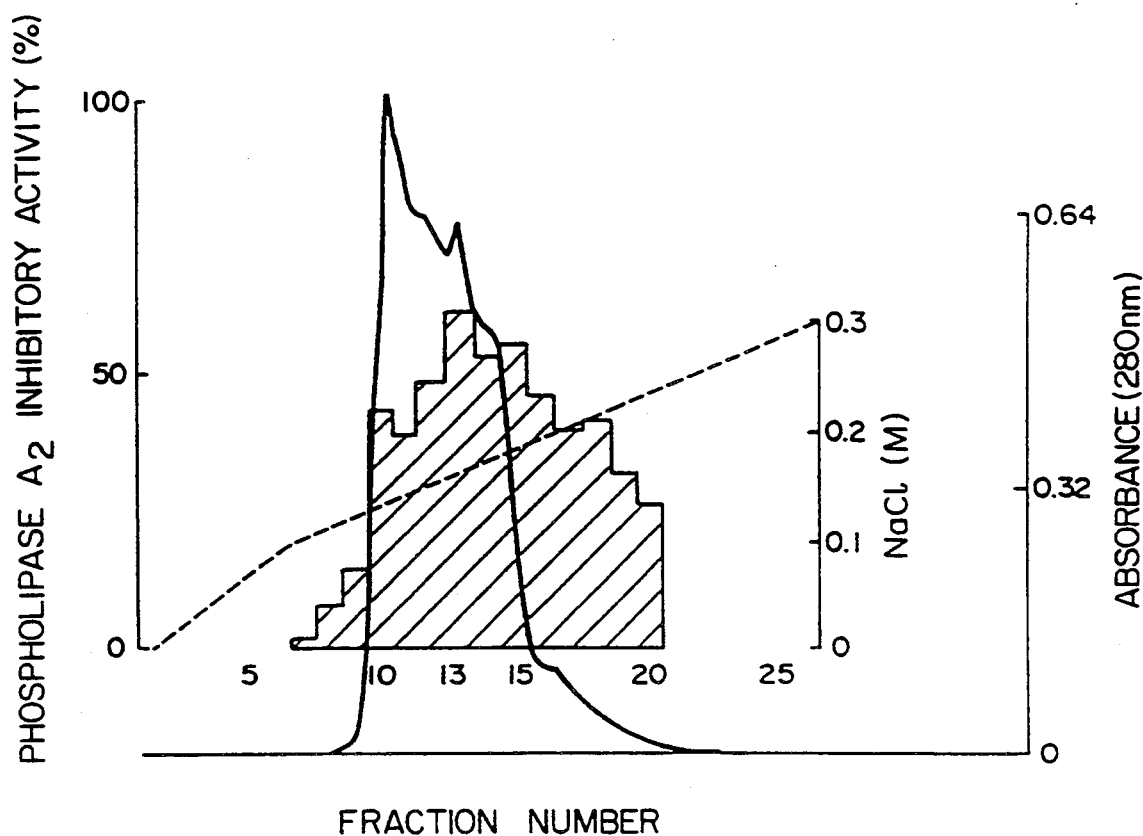

Then, fractions Nr. 52 to 54 in which 39 kDa band was detected in SDS-PAGE among fractions given in FIG. 13b were collected, diluted 4 times and purified with a preparative anion-exchange HPLC column (TSK gel DEAE-5PW) (FIGS. 14a–b). In FIG. 14a, the continuous line draws the UV absorption at 280 nm, the dotted line depicts the gradient of NaCl concentration, and the bar graph shows the inhibitory activity against phospholipase $A_2$ purified from human inflammatory sites.

The purification conditions were 20 mM Tris.HCl, pH 7.5–1 M NaCl (0→1.0 M), 1.0 ml/min. 2 min./tube.

Figure 15A:
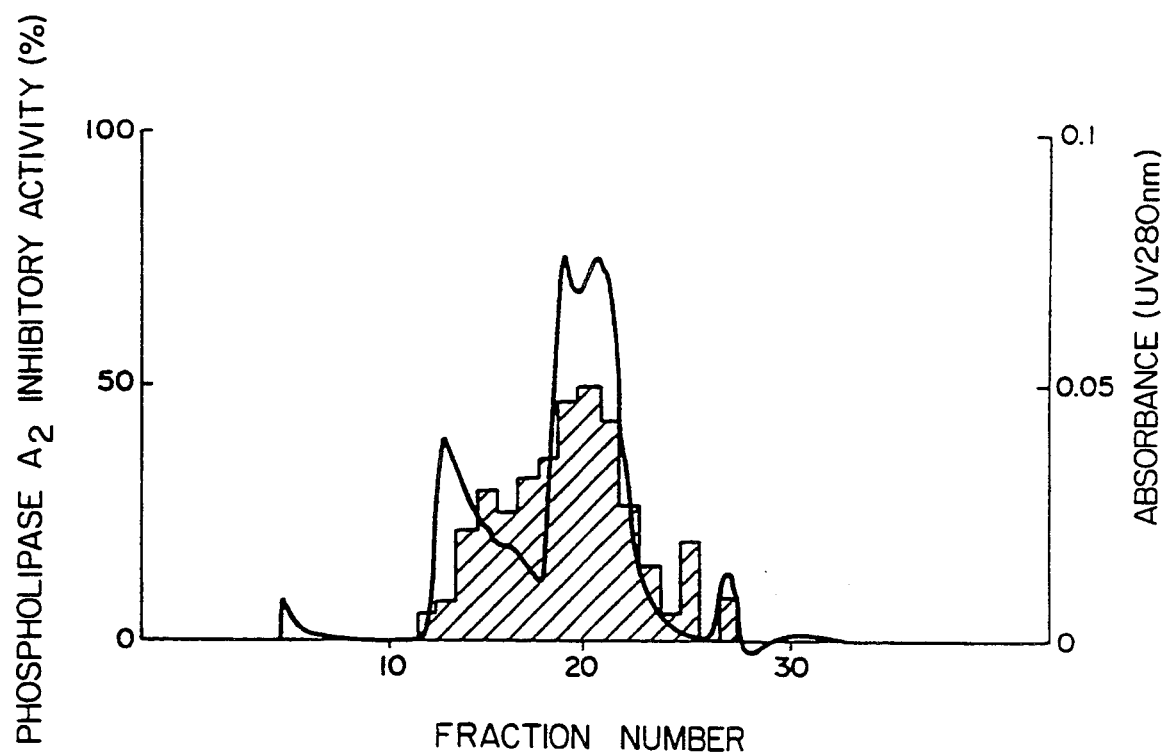

Then, the fraction Nr. 13 in which the 39 kDa band was detected in SDS-PAGE in FIG. 14b and the inhibitory activity against phospholipase $A_2$ purified from human inflammatory sites was strongest was collected and additionally fractionated with a gel filtration HPLC column (TSK gel G3000SW) (FIGS. 15a–b). In FIG. 15a, the continuous line draws the UV absorption at 280 nm, and the bar graph shows the inhibitory activity against phospholipase $A_2$ purified from human inflammatory sites.

The elution conditions were 20 mM Tris.HCl, pH 7.5–1 M NaCl 0.5 ml/min. 2 min./tube.

Figure 16A:
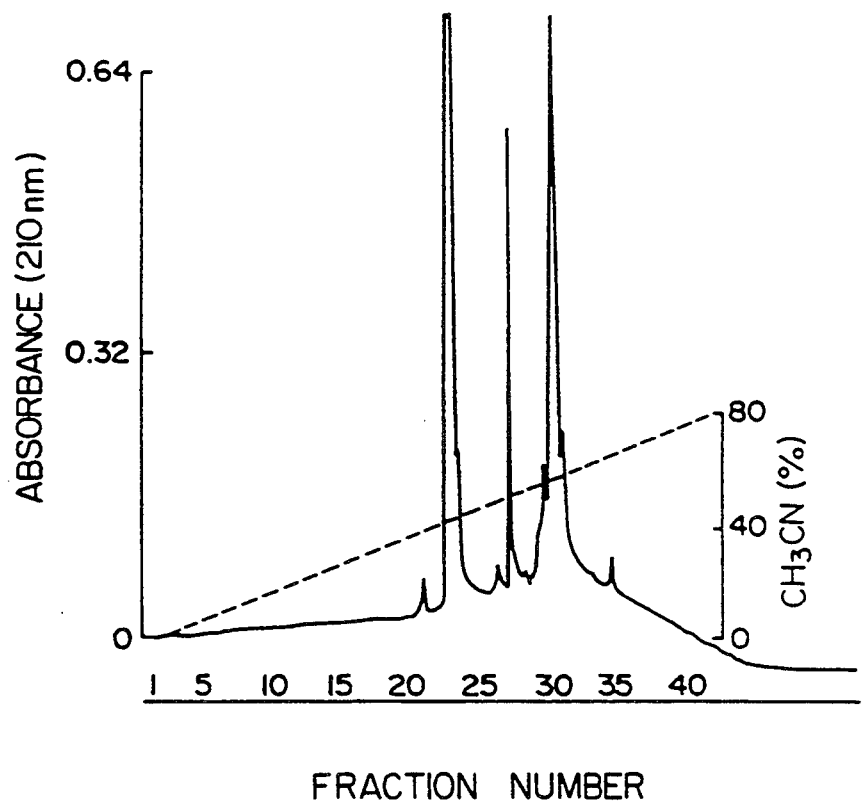

Finally, fractions Nr. 20 and 21 in which the 39 kDa band was detected in SDS-PAGE in FIG. 15b and the inhibitory activity against phospholipase $A_2$ purified from human inflammatory sites was strongest were collected and additionally purified with a reverse phase HPLC column (Bio-Rad RP304) (FIGS. 16a–b). In FIG. 16a, the continuous line draws the UV absorption at 210 nm and the dotted line depicts the gradient of $CH_3CN$ concentration.

The purification conditions were 0.1% $TFA/CH_3CN$ 0 to 80%, ml/min, 2 min/tube.

As shown in SDS-PAGE in FIG. 16b, the inhibitory protein-human of molecular weight 39 kDa was eluted in fraction Nr. 30, but it has been found that the protein is contaminated with a small amount of another protein which was mainly eluted in fraction Nr. 23 and may be albumin. But, albumin does not have strong inhibitory activity against phospholipase $A_2$, and fraction Nr. 23 showed no phospholipase $A_2$-inhibitory activity, either. Thus, it was concluded that they cause no influence on the activity determination of the inhibitory protein.

(B) phospholipase $A_2$-inhibitory activity of inhibitory protein-human

The inhibitory protein-human according to the present invention, obtained in (A), (fraction Nr. 30 in reversed phase HPLC, protein concentration 15 ng/μl) was determined its inhibitory activity against phospholipase $A_2$ purified from human inflammatory site and other phospholipase $A_2$ according to the method described in Example 1.

Figure 17:
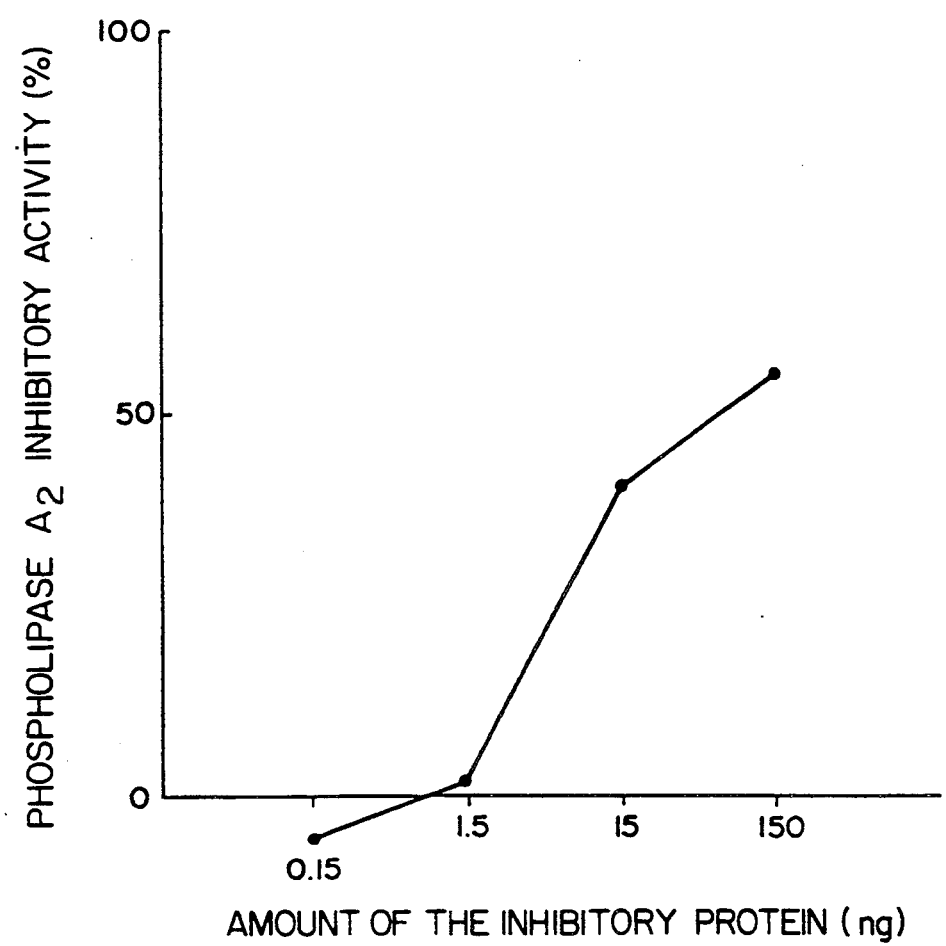
FIG. 17 shows the inhibitory activity of the inhibitory protein-human according to the present invention.

The results are given in FIG. 17 and Table 1.

TABLE 1

| Comparison of inhibitory activity of the inhibitory protein of the invention against various phospholipases $A_2$ | |
|---|---|
| source of phospholipase $A_2$ | the inhibitory activity (%)* against phospholipase $A_2$ |
| synovial fluid from human with rheumatoid arthritis | 47.4 |
| rat platelet (purified from rat inflammatory site) | 22.0 |
| porcine pancreas | 6.5 |

*inhibitory activity when about 15 ng of inhibitory protein-human was added to 1 ng of phospholipase $A_2$.

It is evident from FIG. 17 that the inhibitory protein according to the present invention inhibits phospholipase $A_2$ purified from human inflammatory site in a dose dependent manner. The amount of the inhibitory protein needed for inhibiting 1 ng of phospholipase $A_2$ purified from human inflammatory sites was about 50 ng. As shown clearly in Table 1, the inhibitory protein inhibited phospholipase $A_2$ purified from rat inflammatory sites, but not phospholipase $A_2$ purified from porcine pancreas.

As a result of these facts, it can be concluded that the inhibitory protein according to the present invention has a specific inhibitory activity against phospholipase $A_2$ purified from human inflammatory sites.

EXAMPLE 3

Identification of phospholipase $A_2$-inhibitory protein originating from rat inflammatory sites (A) Determination of N-terminal amino acid sequence in the inhibitory protein-rat The 39 kDa inhibitory protein, which was isolated and purified in Example 1 (A), was determined its N-terminal amino acid sequence by means of the gas-phase protein sequencer 477A (Applied Biosystem Co.). The sequence was as follows:

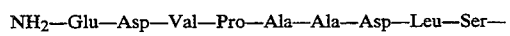
$NH_2$—Glu—Asp—Val—Pro—Ala—Ala—Asp—Leu—Ser—

This sequence was identical completely to the N-terminal sequence of C3dg which is deduced from the base sequence of rat C3 cDNA which will be stated later and was also identical completely to the N-terminal amino acid sequence of the protein inhibitors of phospholipase $A_2$ purified from peritoneal exudate of a rat treated with dexamethasone.

(B) The C-terminal fragment of the inhibitory protein was determined its amino acid sequence as in (A) and the following sequence was obtained:

Gln-Thr-Asp-Val-Pro-Asp-His-Lys-Asp-Leu-Asn-Met-Asp-Val-Ser-Leu-His-Leu-Pro-Ser-Arg.

This sequence was completely identical to the C-terminal sequence of C3dg which is anticipated from the base sequence of rat C3 cDNA which will be stated later.

(C) Western blotting of inhibitory protein-rat

The inhibitory protein-rat of about 39 kDa molecular weight, which was isolated and purified in Example 1 (A), was subjected to SDS-PAGE in a usual manner, and transferred to a nitrocellulose membrane filter using an electroblotting apparatus (Milipore Co.) according to the protocol proposed by Millpore. The filter was stained by the enzyme-linked immunostaining method using rabbit anti-human C3d serum (DAKOPATTS) as a primary antibody, anti-rabbit Ig G horseraddish peroxidase-conjugated sheep Ig G fraction (CAPPEL) as a secondary antibody, and 4-chloro-1-naphthol (Bio-Rad) as a substrate.

As a result, the inhibitory protein specifically reacted with anti-human CSd serum.

From (A), (B) and (C), the inhibitory protein according to the present invention was identified as rat C3dg.

EXAMPLE 4 cDNA cloning of protein inhibitors of phospholipase $A_2$ purified from inflammatory sites (A) Preparation of mouse C3 cDNA segment The Hind III digest of plasmid pFC4/5.4 containing mouse C3 cDNA segment (J. B.C. 260, 10936, 1986) was subjected to the low-melting agarose gel electrophoresis to separate the 2.2 kbp segment. Further, Stu I digest was subjected to similar operations to give 1.8 kbp segment.

(B) Screening of cDNA

Screening was performed using rat liver cDNA λ gt 11 library (Clone Tech Co.) according to the manual of the experimental protocol by the Clone Tech.

In other words, *E. coli* 1090 line infected with λ gt 11 phage was cultured at 37° C. for 5 hours and the resultant about 50,000 transformants were replicated to a nylon filter membrane, dipped in 0.5 M NaOH–1.5 M NaCl to modify the DNA, and neutralized with Tris.HCl buffer containing 1.5 M NaCl-1 mM EDTA (pH 7.2). Then, the filter was air-dried, and the DNA was immobilized to the filter by irradiating with ultraviolet rays for 3 minutes using a trans-illuminator. The mouse C3 cDNA obtained in (A) was labeled with $^{32}p$, and used as a screening probe.

The transformant groups on the examined filter were screened by hybridization with the probe at 65° C. and the hybridization was judged by the autoradiography and 7 transformants were found to be positively cloned among about 50,000 transformants. These positive clones were named λ r C3/11-17.

These clones were digested with EcoRI, then agarose gel electrophoresis was conducted to analyze the chain length of the inserted gene segment according to southern hybridization. The inserted DNA of γλ C3/11 was longest among these seven clones and it was found to have the insertion gene segment of 2.7 kbp total length which is digested into 0.7 kbp and 2.0 kbp segments by EcoRI.

(C) Determination of base sequence of rat C3 cDNA

After phage DNA of γλ C3/11 was extracted, the DNA was digested with EcoRI to give 0.7 kbp and 2.0 kbp DNA segments. These segments were inserted into the EcoRI sites of M13mp19 (TAKARA SHUZO). The 0.7 kbp segment was further digested with BamHI into 0.1 kbp segment and 0.6 kbp segment, and these segments were inserted into the mp19 to determine the base sequence from both ends.

The sequence was analyzed according to the 7-DEAZA technique [Mizusawa, et al., Nucleic Acid Res., 14, 1319 (1986)]. The 2.0 kbp segment was analyzed according to the technique developed by Hood et al in which the sequence analysis is put forward, as the primers designed from the determined region are synthesized [Hood, et al., Anal. Biochem., 154, 353 (1986)].

Figure 18:
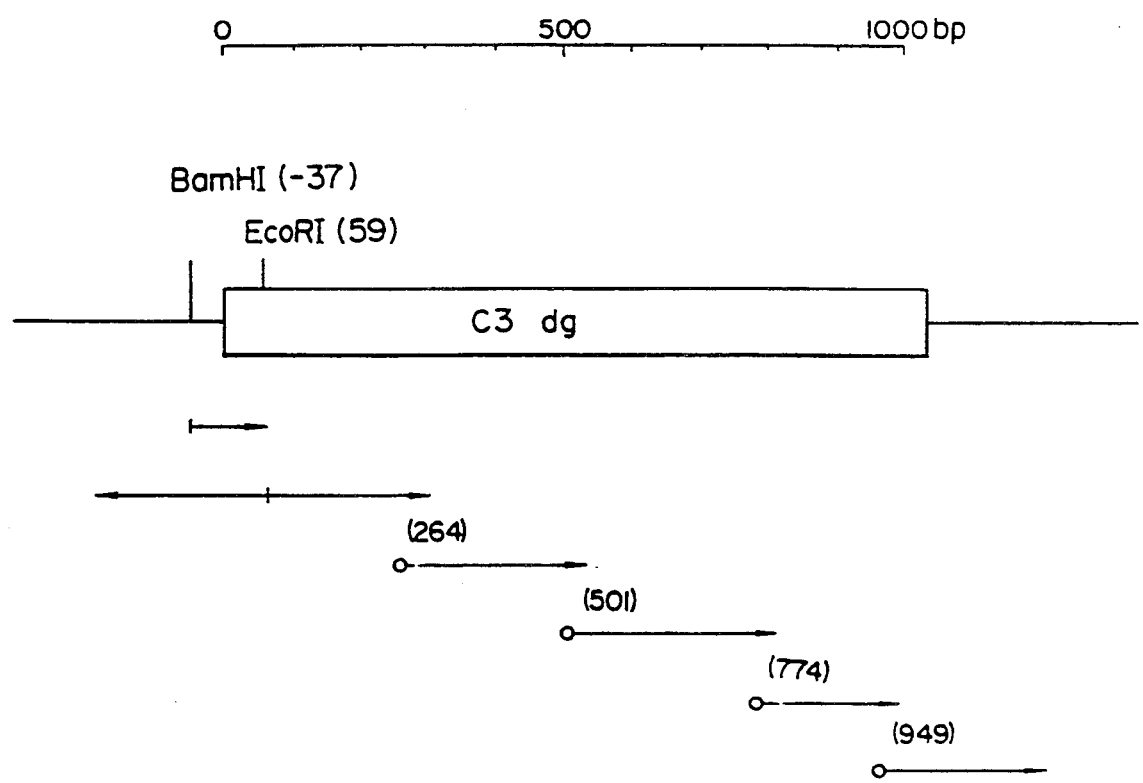
FIG. 18 shows the strategy for determining the base sequence of the gene containing the inhibitory protein-rat according to the present invention.

The strategy for determining the base sequence of λ r C3/11 is given in FIG. 18. In the Figure, the uppermost numerals are the base numbers at the breakage points based on the framed part of rat C3dg, EcoRI and others are the names of restriction enzymes and the numerals in parentheses are the base number on the cleavage site or the starting site for determination of base sequence. The horizontal arrows give the direction and range for determining base sequence with restriction enzymes and the primer, respectively.

EXAMPLE 5

Determination of the base sequence of the gene coding protein inhibitors of phospholipase $A_2$ purified from rat inflammatory sites and the amino acid sequence of the protein (1) Determination of N-terminal and C-terminal FIGS. 19a–b show the part corresponding to the amino acid sequence in the neighborhood of the breakage sites by human C3 factor I, among the rat C3 amino acid sequence presumed from the base sequence (C) of the C3 cDNA clone which has been elucidated in Example 4.

Human C3 is cleaved by factor I between $^{283}$Arg-$^{284}$Glu in the α chain, but the corresponding site shifts to Gln-Gly in rat C3 and Arg-Glu exists at the site five residues after Gln-Gly. And, the N-terminal amino acid sequence of the fragment formed by cleavage at this site was completely identical to the N-terminal amino acid sequence of the inhibitory protein according to the invention, which was purified from rat serum.

Accordingly, it is thought that rat C3 is cleaved at this site by an enzyme having similar activity to human factor I.

In the meantime, $^{632}$Arg-$^{633}$Ser and $^{649}$Arg-$^{650}$Ser in human C3 α chain were consevedin rat C3, too. Further, the C-terminal amino acid sequence of the fragment formed by cleavage at this side was completely identical to the C-terminal amino acid sequence of the inhibitory protein according to the present invention, purified from rat serum. As in human C3, rat C3 is presumably cleaved at these sites by factor I and the C-terminal of the inhibitory protein according to the present invention was identical to the C-terminal of human C3dg.

(2) The complete base sequence of the gene of protein inhibitors of phospholipase $A_2$ purified from rat inflammatory sites and deduced complete amino acid sequence On the basis on these results, the complete amino acid sequence of the protein inhibitor of phospholipase $A_2$ purified from inflammatory sites and the complete base sequence of the gene according to the present invention can be given in FIGS. 1-1-1-3 and FIGS. 2-1-2-3. The protein inhibitor of phospholipase $A_2$ purified from inflammatory sites has been found to be a protein which is coded with 1032 bases and is composed of 344 amino acids.

EXAMPLE 6

Determination of the complete base sequence of the gene of protein inhibitors of phospholipase $A_2$ purified from human inflammatory sites and the complete amino acid sequence of the inhibitory protein (A) Identification of inhibitory protein-human (1) Determination of the N-terminal amino acid sequence of inhibitory protein-human The N-terminal amino acid sequence was determined in the same manner as described above on the inhibitory protein of about 39 kDa molecular weight which was isolated and purified in Example 2(A) (fraction Nr. 30 in the reverse phase HPLC). As a result, the following sequence was given:

NH2—Glu—Gly—Val—Asn—Lys—Glu—Asp—Ile—Pro—Pro—

This sequence was completely identical to the N-terminal amino acid sequence of human C3dg.

(2) Immunochemical analysis of inhibitory protein-human

After the inhibitory protein of about 39 kDa molecular weight which was isolated and purified in Example 2(A) (fraction Nr. 30 in reverse phase HPLC) was subjected to SDS-PAGE, the protein was transferred to a filter by the western blotting method and detected by the enzyme-linked immunostaining method using anti-human C3d serum. As a result, the inhibitory protein according to the present invention reacted with anti-human C3d serum specifically. FIG. 20a gives the SDS-PAGE, while FIG. 20b shows the western blotting.

The results from (1) and (2) evidently reveals that the inhibitory protein according to the present invention is human C3dg.

(B) The complete base sequence of the gene of protein inhibitors of phospholipase $A_2$ purified from human inflammatory sites (C3 dg) and the complete amino acid sequence of the inhibitory protein cDNA cloning of human C3 was already established and the complete base sequence and the complete amino acid sequence deduced therefrom were determined. Further, the part coding C3dg was also decided in the C3 gene [de Brujin et al., Proc. Natl. Acd. Sci. USA, 82, 708–712 (1985)].

The results described above evidently show that the protein inhibitors of phospholipase $A_2$ purified from human inflammatory sites is human C3dg. Accordingly, the base sequence of the inhibitory protein of this invention is presumed to be completely identical to the part coding C3dg in the entire base sequence of the human C3 gene.

Consequently, it was judged that the complete amino acid sequence of the protein inhibitor of phospholipase $A_2$ purified from human inflammatory sites and the complete base sequence of the protein inhibitor of phospholipase $A_2$ purified from human inflammatory sites of the invention are those given in FIG. 3 and FIG. 4, respectively. The protein inhibitors of phospholipase $A_2$ purified from inflammatory sites was found to be a protein which is coded with 1047 bases and comprises 349 amino acids.

We claim:

1. A process for preparing a phosphilipase $A_2$-inhibitory protein consisting of the amino acid sequence of FIGS. 3–1 through 3—3 comprising:
   (a) obtaining human serum;
   (b) incubating said serum at 37° C. for 6 to 10 days;
   (c) adding a protease inhibitor to said incubated serum; and
   (d) purifying said inhibitory protein from said serum.

2. Protein inhibitors of phospholipase $A_2$ purified from inflammatory sites wherein said inhibitors consist of the amino acid sequence given in FIGS. 3-1 through 3-3.

* * * * *